(12) United States Patent
Auvray et al.

(10) Patent No.: US 10,664,970 B2
(45) Date of Patent: May 26, 2020

(54) APPARATUS AND METHOD OF AUTOMATIC PRE AND POST QUANTITATIVE CORONARY ANGIOGRAPHY FOR QUALIFYING AN OUTCOME OF A VASCULAR TREATMENT

(71) Applicant: KONINKLIJKE PHILIPS N.V., Eindhoven (NL)

(72) Inventors: Vincent Maurice André Auvray, Meudon (FR); Olivier Pierre Nempont, Suresnes (FR); Guillaume Julien Joseph Pizaine, Issy-les-Moulineaux (FR); Raoul Florent, Ville d'Avray (FR)

(73) Assignee: KONINKLIJKE PHILIPS N.V., Eindhoven (NL)

(*) Notice: Subject to any disclaimer, the term of this patent is extended or adjusted under 35 U.S.C. 154(b) by 189 days.

(21) Appl. No.: 15/747,585

(22) PCT Filed: Jul. 14, 2016

(86) PCT No.: PCT/EP2016/066740
§ 371 (c)(1),
(2) Date: Jan. 25, 2018

(87) PCT Pub. No.: WO2017/016885
PCT Pub. Date: Feb. 2, 2017

(65) Prior Publication Data
US 2018/0211389 A1    Jul. 26, 2018

(30) Foreign Application Priority Data

Jul. 27, 2015 (EP) .................................. 15306216

(51) Int. Cl.
G06T 7/00      (2017.01)
A61B 6/12      (2006.01)
(Continued)

(52) U.S. Cl.
CPC ............ *G06T 7/0016* (2013.01); *A61B 6/032* (2013.01); *A61B 6/12* (2013.01); *A61B 6/4441* (2013.01);
(Continued)

(58) Field of Classification Search
None
See application file for complete search history.

(56) References Cited

U.S. PATENT DOCUMENTS

| 2011/0081057 A1* | 4/2011 | Zeng ............... G06T 7/0012 382/128 |
| 2016/0213896 A1* | 7/2016 | Bacallao ............. A61B 5/0215 |
| 2018/0211389 A1* | 7/2018 | Auvray ................ A61B 6/481 |

OTHER PUBLICATIONS

Bredno, J. et al "Algorithmic Solutions for Live Device-to-Vessel Match". Proceedings of SPIE, vol. 5370—Medical Imaging 2004: Image Processing, pp. 1486-1497.
(Continued)

*Primary Examiner* — Tahmina N Ansari (57) ABSTRACT

The present invention relates to apparatus for automatic quantification of a part of vascular structure. It is described to provide (12) at least one first image comprising a spatial representation of a region of interest of a vascular structure, wherein the at least one first image comprises image data representative of a location of a part of a medical device. The medical device is configured to be used in a vascular treatment, and the part of the medical device is configured to be in a plurality of states associated with different phases of the vascular treatment. At least one second image comprising a spatial representation of the region of interest of the vascular structure is provided (14), wherein the at least one second image comprises image data representative of at least a part of the vascular structure in a visible and distinct manner. A location of a feature in the spatial representation of the region of interest of the vascular structure of the at
(Continued)

least one first image is determined (18), wherein the feature is associated with the part of the medical device in one of the states associated with a phase of the vascular treatment. A transform relating at least one location in the at least one first image to a corresponding at least one location in the at least one second image is determined (20) and applied to the location of the feature in the spatial representation of the region of interest of the vascular structure of the at least one first image to provide a determined location in the spatial representation of the region of interest of the vascular structure of the at least one second image. Data is output (22) representative of the vascular structure at the determined location.

11 Claims, 4 Drawing Sheets

(51) Int. Cl.
| | | |
|---|---|---|
| *G16H 50/50* | (2018.01) | |
| *A61B 6/00* | (2006.01) | |
| *G06T 7/30* | (2017.01) | |
| *A61M 25/10* | (2013.01) | |
| *G16H 40/63* | (2018.01) | |
| *A61B 6/03* | (2006.01) | |
| *G16H 30/40* | (2018.01) | |
| *A61F 2/95* | (2013.01) | |
| *G06T 3/00* | (2006.01) | |
| *A61B 5/107* | (2006.01) | |
| *A61B 90/00* | (2016.01) | |
| *A61B 5/00* | (2006.01) | |
| *A61B 17/22* | (2006.01) | |

(52) U.S. Cl.
CPC .............. *A61B 6/481* (2013.01); *A61B 6/486* (2013.01); *A61B 6/487* (2013.01); *A61B 6/503* (2013.01); *A61B 6/504* (2013.01); *A61B 6/5217* (2013.01); *A61B 6/5235* (2013.01); *A61B 6/5264* (2013.01); *A61B 6/5288* (2013.01); *A61F 2/95* (2013.01); *A61M 25/104* (2013.01); *G06T 3/0068* (2013.01); *G06T 7/0012* (2013.01); *G06T 7/30* (2017.01); *G16H 30/40* (2018.01); *G16H 40/63* (2018.01); *G16H 50/50* (2018.01); *A61B 5/1076* (2013.01); *A61B 5/4848* (2013.01); *A61B 2017/22001* (2013.01); *A61B 2090/364* (2016.02); *A61B 2090/376* (2016.02); *G01N 2800/323* (2013.01); *G06T 2207/10081* (2013.01); *G06T 2207/10121* (2013.01); *G06T 2207/30021* (2013.01); *G06T 2207/30101* (2013.01); *G06T 2211/404* (2013.01)

(56) References Cited

OTHER PUBLICATIONS

"ACC/AHA/SCAI 2014 Health Policy Statement on Structured Reporting for the Cardiac Catheterization Laboratory". Timothy A. Sanborn, et al. In Journal of the American College of Cardiology, vol. 63, issue 23, Jun. 2014.

Tobis, Jonathan et al "Digital Coronary Roadmapping as an Aid for Performing Coronary Angioplasty", American Journal of Cardiology, vol. 56, No. 4, 1985, pp. 237-241.

Reiber, Johan H.C. et al "QCA, IVUS and OCT in Interventional Cardiology in 2011", Cardiovascular Diagnosis and Therapy, pp. 57-70. 2011.

Tomasello, Salvatore Davide et al "Quantitative Coronary Angiography in the Interventional Cardiology", Advances in the Diagnosis of Coronary Atherosclerosis, No. 2011.

\* cited by examiner

APPARATUS AND METHOD OF AUTOMATIC PRE AND POST QUANTITATIVE CORONARY ANGIOGRAPHY FOR QUALIFYING AN OUTCOME OF A VASCULAR TREATMENT

CROSS-REFERENCE TO PRIOR APPLICATIONS

This application is the U.S. National Phase application under 35 U.S.C. § 371 of International Application No. PCT/EP2016/066740, filed on Jul. 14, 2016, which claims the benefit of European Patent Application No. 15306216.1, filed on Jul. 27, 2015. These applications are hereby incorporated by reference herein.

FIELD OF THE INVENTION

The present invention relates to an apparatus for automatic quantification of a part of vascular structure, to a medical system for automatic quantification of a part of a vascular structure, and to a method for automatic quantification of a part of a vascular structure, as well as to a computer program element and a computer readable medium.

BACKGROUND OF THE INVENTION

In vascular treatments, for example in Percutaneous Transluminal Coronary Angioplasty (PTCA) to treat cardiac stenosis, information relating to the vascular treatments is required to be provided. In particular, the clinician has to describe which stenosis was treated, for instance by localizing them onto a schematic graph of the coronary arteries. Furthermore, Quantitative Coronary Angiography (QCA) values of each stenosis before and after stenting are often required to be provided. US 2011/0081057A1 relates to a QCA system. The QCA value is the relative reduction of the artery diameter at the stenosis position. These values can be used to support the need for intervention, and to document the success or failure of the intervention. The clinician frequently has to select a sequence of angiograms obtained pre-intervention, i.e. before the actual intervention or treatment, and to select a frame from that sequence, to locate the stenosis, and to click several times on the frame with the mouse cursor in order to determine a QCA value. This also has to be conducted for a sequence of angiograms obtained post-intervention, ie. after the intervention or treatment. Therefore, obtaining QCA values takes time, can be tedious, and as such is sometimes omitted or only roughly estimated visually.

Tobias J., et al, American Journal of Cardiology, vol. 56, n. 4, (1985) pages 237-241, describe digital coronary roadmapping as an aid for performing coronary angioplasty.

SUMMARY OF THE INVENTION

It would be advantageous to have an improved technique for providing quantitative coronary angiography values.

The object of the present invention is solved with the subject matter of the independent claims, wherein further embodiments are incorporated in the dependent claims. It should be noted that the following described aspects of the invention apply also for the apparatus for automatic quantification of a part of a vascular structure, the medical system for automatic quantification of a part of vascular structure, the method for automatic quantification of a part of a vascular structure, and for the computer program element and the computer readable medium.

According to a first aspect, there is provided an apparatus for automatic quantification of a part of a vascular structure, the apparatus comprising:

an input unit;
a processing unit; and
an output unit.

The input unit is configured to provide the processing unit with at least one first image comprising a spatial representation of a region of interest of a vascular structure. The at least one first image comprises image data representative of a location of a part of a medical device, wherein the medical device is configured to be used in a vascular treatment, and wherein the part of the medical device is configured to be in a plurality of states associated with different phases of the vascular treatment. The input unit is also configured to provide the processing unit with at least one second image comprising a spatial representation of the region of interest of the vascular structure. The image data is representative of at least a part of the vascular structure in a visible and distinct manner. The processing unit is configured to determine a location of a feature in the spatial representation of the region of interest of the vascular structure of the at least one first image, wherein the feature is associated with the part of the medical device in one of the states associated with a phase of the vascular treatment. The processing unit is also configured to determine a transform relating at least one location in the at least one first image to a corresponding at least one location in the at least one second image, and to apply the transform to the location of the feature in the spatial representation of the region of interest of the vascular structure of the at least one first image to provide a determined location in the spatial representation of the region of interest of the vascular structure of the at least one second image. The output unit is configured to output data representative of the vascular structure at the determined location.

As a result, pre-intervention and post-intervention QCA values are enabled to be determined. Furthermore, QCA values at the time of the intervention can also be determined. This enables for it to be determined whether the intervention was carried out as expected, whether the intervention was successful, whether the intervention was deployed as expected, and whether the post-intervention vascular structure is as expected.

In an example, the vascular treatment was applied at a time corresponding to a time of acquisition of the at least one first image. The processing unit is configured to determine from the at least one first image that the vascular treatment was applied at the time of acquisition of the at least one first image. By determining the time when the vascular treatment was applied it can be determined whether the at least one second image was acquired before or after the time of the vascular treatment, or that the vascular treatment was applied at the time of acquisition of the at least one second image. In other words, the at least one second image can be automatically placed into temporal context with respect to the vascular treatment.

In an example, the processing unit is configured to align the spatial representation of the region of interest of the vascular structure in the at least one first image with the spatial representation of the region of interest of the vascular structure in the at least one second image in order to determine and apply the transform.

The term "determine a transform relating at least one location in the at least one first image to a corresponding at least one location in the at least one second image" can also mean correlating a location in the spatial representation of the region of interest of the vascular structure of the at least one first image with a correlated location in the spatial representation of the region of interest of the vascular structure of the at least one second image, and can also mean registering the first image with the second image in order to relate a location in the first image with a location in the second image.

According to a second aspect, there is provided a medical system for automatic quantification of a part of a vascular structure, the system comprising:

at least one image acquisition unit; and an apparatus for automatic quantification of a part of a vascular structure according to any of the preceding examples.

The at least one image acquisition unit is configured to provide the at least one first image comprising the spatial representation of the region of interest of the vascular structure, and to provide the at least one second image comprising the spatial representation of the region of interest of the vascular structure. By providing a medical system for automatic quantification of a part of a vascular structure, such as at the location of an anomaly or stenosis, pre and post intervention the clinician is automatically provided with the required reporting information associated with the intervention. The clinician is provided with information regarding which stenosis was treated, and where that stenosis is located within the vascular structure. They are provided with information regarding the severity of a stenosis prior to the intervention, and whether the intervention has been successful. They do not need to manually determine QCA values relating to the intervention, which would require a manual determination of when the intervention was performed and assessing angiography (angio) image frames both before and after that intervention, and which would also require a manual determination of where the intervention was performed within those images.

According to a third aspect, there is provided a method for automatic quantification of a part of a vascular structure, comprising:

a) providing at least one first image comprising a spatial representation of a region of interest of a vascular structure, wherein the at least one first image comprises image data representative of a location of a part of a medical device, wherein the medical device is configured to be used in a vascular treatment, and wherein the part of the medical device is configured to be in a plurality of states associated with different phases of the vascular treatment;

b) providing at least one second image comprising a spatial representation of the region of interest of the vascular structure, wherein the at least one second image comprises image data representative of at least a part of the vascular structure in a visible and distinct manner;

d) determining a location of a feature in the spatial representation of the region of interest of the vascular structure of the at least one first image, wherein the feature is associated with the part of the medical device in one of the states associated with a phase of the vascular treatment;

e) determining a transform relating at least one location in the at least one first image to a corresponding at least one location in the at least one second image, and applying the transform to the location of the feature in the spatial representation of the region of interest of the vascular structure of the at least one first image to provide a determined location in the spatial representation of the region of interest of the vascular structure of the at least one second image; and f) outputting of data representative of the vascular structure at the determined location.

As a result, the at least one second image can be automatically placed into spatial context with respect to the vascular treatment and stenosis. QCA values can then be determined from the at least one second image with respect to the stenosis, and this can be conducted both pre and post stenting. In other words, it is not the feature, per se, in the at least one first image that is instrumental for determining a corresponding location in the at least one second image—only its position matters.

In an example, step d) comprises determining the location of the image data representative of the location of the part of the medical device in the at least one first image. Determining a location of a part of a medical device at a location in the vascular structure can help in determining that there is an anomaly or stenosis at that location.

In an example, the image data representative of the location of the part of the medical device comprises non-injected X-ray data.

In an example, the non-injected X-ray data comprises fluorescence image data.

In an example, the image data representative of the location of the part of the medical device comprises fluorescence image data. Therefore, standard procedures and equipment can be used, such as that utilizing fluoroscopic X-ray equipment.

In an example, the vascular treatment was applied at a time corresponding to a time of acquisition of the at least one first image, and the method further comprises the following step:

c) determining from the at least one first image that the vascular treatment was applied at the time of acquisition of the at least one first image.

By determining the time when the vascular treatment was applied, it can be determined whether the at least one second image was acquired before or after the time of the vascular treatment, or that the vascular treatment was applied at the time of acquisition of the at least one second image. In other words, the at least one second image can be automatically placed into temporal context with respect to the vascular treatment.

In an example, the vascular treatment comprises the part of the medical device being moved from a non-deployed state to a deployed state, and the at least one first image comprises image data representative of the part of the medical device in a state other than the non-deployed state.

Therefore, deployment of the medical device can be used to determine the location of the feature and determine the time of the vascular treatment. Thus, the deployment of the medical device can be used to place the at least one second image into spatial and temporal context with respect to an anomaly or stenosis and its treatment. In an example, step e) comprises:

e1) aligning the spatial representation of the region of interest of the vascular structure in the at least one first image with the spatial representation of the region of interest of the vascular structure in the at least one second image.

This means, for example, that cardiac road-mapping can be used in determining the transform and can be used in applying the transform.

In an example, step e1) comprises determining a region of reduced vessel radius in a region in or around the determined location in the spatial representation of the region of interest of the part of the vascular structure of the at least one second image.

As a result, this provides for fine-tuning of the aligning process, for example if the stenosis position translated from its detection in the at least one first image and the at least one second image to at least one first image matching is not as accurate as required.

In an example, the at least one first image comprises image data representative of the part of a medical device located within a part of the vascular structure; and step e1) further comprises aligning the image data representative of the part of the medical device located within the part of the vascular structure in the at least one first image with the spatial representation of the region of interest of the part of the vascular structure in the at least one second image.

As a result, the medical device itself can be used within a cardiac road-mapping technique, enabling the transform to be determined.

According to another aspect, there is provided a computer program element controlling apparatus as previously described which, in the computer program element is executed by processing unit, is adapted to perform the method steps as previously described.

According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
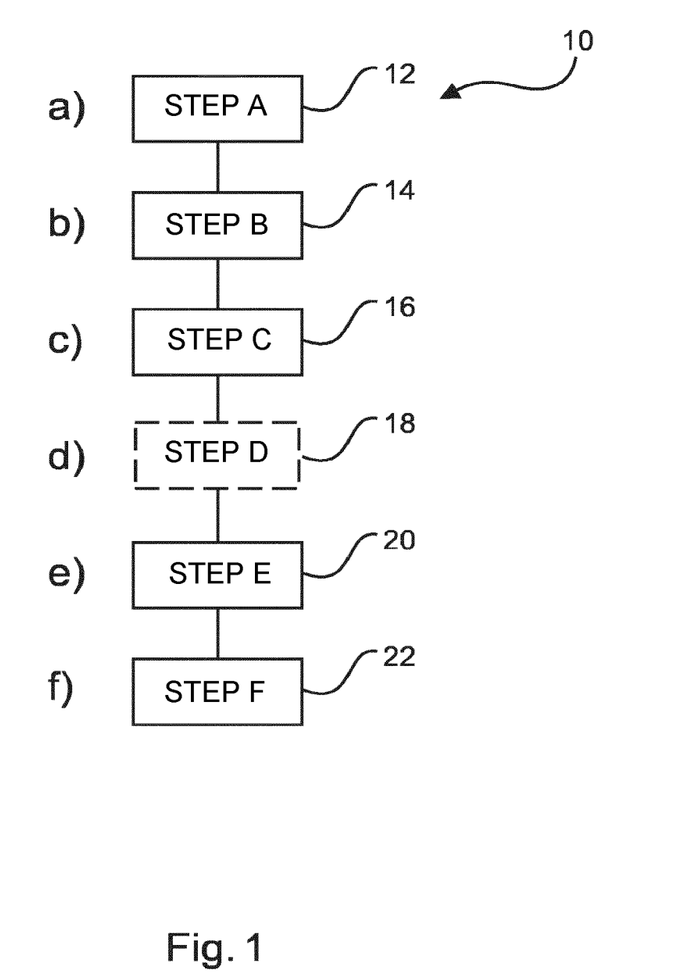
FIG. 1 shows an example of a method for automatic quantification of a part of a vascular structure.

FIG. 1 shows a method 10 for automatic quantification of a part of a vascular structure in its basic step. The method comprises the following:

In a first providing step 12, also referred to as step a), at least one first image comprising a spatial representation of a region of interest of a vascular structure is provided. The at least one first image comprises image data representative of a location of a part of a medical device. The medical device is configured to be used in a vascular treatment, and the part of the medical device is configured to be in a plurality of states associated with different phases of the vascular treatment.

In a second providing step 14, also referred to as step b), at least one second image comprising a spatial representation of the region of interest of the vascular structure is provided. The at least one second image comprises image data representative of at least a part of the vascular structure in a visible and distinct manner.

In a first determining step 18, also referred to as step d), a location of a feature in the spatial representation of the region of interest of the vascular structure of the at least one first image is determined. The feature is associated with the part of the medical device in one of the states associated with a phase of the vascular treatment.

In a second determining step 20, also referred to as step e), a transform relating at least one location in the at least one first image to a corresponding at least one location in the at least one second image is determined. Step 20 also involves applying the transform to the location of the feature in the spatial representation of the region of interest of the vascular structure of the at least one first image to provide a determined location in the spatial representation of the region of interest of the vascular structure of the at least one second image.

In an outputting step 22, also referred to as step f), data representative of the vascular structure at the determined location is output.

The term "visible and distinct" with respect to the at least a part of the vascular structure relates to at least part of the vascular structure being presented such that the vascular structure can be located or identified or delineated, either manually or automatically, or any combination of these. For example, the determined location in the at least one second image is presented in a visible and distinct manner.

In an example, the vascular structure is not visible and distinct within the at least one first image. For example, the at least one first image was acquired during fluoroscopic low-dose X-ray surveillance.

In an example, the at least one second image is of an image type different to the at least one first image. In an example, the at least one first image is not an angiogram.

The term "angiogram" relates to a visualization of the blood vessels of the heart region, and, alternatively or in addition, a vascular structure outside of the heart of the patient.

In an example, the at least one second image is based on X-ray radiation.

In an example, contrast agent is present during the acquisition of the at least one second image. For example, contrast agent has been injected into at least a part of the vascular structure in order to provide image data of the vascular structure in a visible and distinct manner. In an example, the at least one second image is an angiogram.

In an example, the at least one first image is acquired in the manner of an angiogram, but where no, or little, contrast agent has been injected into at least a part of the vascular structure during acquisition of the image. In other words, the method can involve an imaging system acquiring a number of similar images, which at the time contrast agent is injected are acquired as second image(s) and at the time when no (or little) contrast agent is injected are acquired as first image(s).

In an example, the part of the medical device configured to be in a plurality of states associated with different phases of the vascular treatment means that the part of the medical device can be at a particular location within the patient's vascular structure. For example, the part of the medical device can be within an artery at the location of a stenosis. Or the part of the medical device can be at the position of the stenosis and can be used in carrying out an operation relating to the treatment of the stenosis.

In an example, at the determined location, a stenosis is well-visible within the at least one second image acquired pre-treatment.

In an example, at the determined location, a stented stenosis is well-visible within the at least one second image acquired post-treatment. The term "well-visible" relates to the vascular structure at the determined location being present within the at least one second image such that it can be identified, either manually or automatically. In an example, the term "well-visible" relates to the vascular structure at the determined location being susceptible to quantitative analysis, such as QCA at that location.

In an example, the at least one second image comprises a plurality of second images acquired before a vascular treatment was applied. Step b) then further comprises selecting one of these second images on the basis of at least one of the group of: the image that constitutes the best injected imagery; and the image that constitutes the best injected imagery around the vascular structure at the determined location or stenosis of interest; and the image that was acquired at a time closest to the time of the vascular treatment.

In an example, the at least one second image comprises a plurality of second images acquired after a vascular treatment was applied. Step b) then further comprises selecting one of these second images on the basis of at least one of the group of: the image that constitutes the best injected imagery; and the image that constitutes the best injected imagery around the vascular structure at the determined location or stenosis of interest; and the image that was acquired at a time closest to the time of the vascular treatment.

In example, the at least one second image comprises a plurality of images, and step b) further comprises selecting the image where the vascular structure at the determined location or stenosis appears the longest (or in other words there is minimal foreshortening).

In an example, step d) comprises determining first image coordinates for the location of the feature, and step e) comprises determining second image coordinates for the vascular structure at the determined location.

In an example, the feature is shown in the at least one first image in a visible and distinct manner. For example, a part of the vascular structure, at the location of a stenosis after a stent has been applied, is clearly visible as a stented section of the vascular structure. In another example, the image data representative of a location of a part of a medical device is such that the part of the medical device is shown in a visible and distinct manner.

In an example, the vascular treatment is applied at the location of a stenosis in the vascular structure. For example, by determining and applying the transform the location of the vascular treatment and therefore the location of the stenosis in the at least one second image can be determined. In other words, the at least one second image can be automatically placed into spatial context with respect to the vascular treatment and stenosis. QCA values can then be determined from the at least one second image with respect to the stenosis, and this can be conducted both pre and post stenting. In other words, it is not the feature, per se, in the at least one first image that is instrumental for determining a corresponding location in the at least one second image—only its position matters.

In an example, step e) comprises correlating the location of the feature in the spatial representation of the region of interest of the vascular structure of the at least one first image with a correlated location in the spatial representation of the region of interest of the vascular structure of the at least one second image.

In an example, the feature results from an operation of the part of the medical device.

In an example, step f) comprises outputting of data representative of the vascular structure at the determined position on the at least one second image.

In an example, the medical device being configured to be in a plurality of states comprises a balloon being moved, positioned and inflated/not inflated. For example, a deflated balloon is first introduced by being slid into an artery. Then it is moved to the position of a stenosis. When the balloon in inflated (where the treatment occurs), then the location of the stenosis is precisely known.

According to an example, step d) comprises determining the location of the image data representative of the location of the part of the medical device in the at least one first image.

In an example, the medical device comprises a flexible, partially or fully opaque guidewire that has been inserted into the vascular structure and advanced to the region of interest of the vascular structure.

In an example, the guidewire has been inserted such that a part of it is at the position of an anomaly or stenosis. In other words, the feature is the guidewire, or, alternatively or in addition, the anomaly or stenosis. For example, determining the location of the part of the guidewire at the location of the anomaly serves to locate the position of an anomaly or stenosis in the vascular structure. For example, the end part, or part of the guidewire with a balloon is guided and located and then inflated. In other words, determining a location of a part of a medical device at a location in the vascular structure serves to help in determining that there is an anomaly or stenosis at that location. For example, image processing of a first image may be configured to determine that there is a possibility of an anomaly or stenosis at a particular location. However, when a part of a medical device is also at that location, the image processing is configured to determine that there is an anomaly or stenosis at that location.

In an example, the medical device comprises an interventional device, and the guidewire serves as a rail to deliver the interventional device. For example, the medical device can comprise a catheter. For example, the interventional device can comprise a balloon for dilatation and stent delivery.

In an example, the balloon is configured to contain contrast agent, and wherein determining the location of the image data representative of the location of the part of the medical device comprises detecting the location of the balloon. For example, the balloon is inflated in order to crush a stenosis, and deliver a stent. Once inflated, the balloon contains contrast agent and this is helpful in practice to see and detect the balloon.

In an example, the interventional device has been delivered to the position of an anomaly or stenosis. For example, determining the location of the interventional device at the location of the anomaly serves to locate the position of the anomaly in the vascular structure. In other words, the medical device can be detected from the at least one first image and used to locate the anomaly or stenosis even though the anomaly or stenosis is not itself well-visible within that particular image. In an example, both the anomaly or stenosis and the part of the medical device are visible to a certain degree and both serve to locate the anomaly or stenosis within the vascular structure.

In other words, the feature can be the vascular structure at the location of the part of the medical device, or the feature can be the part of the medical device at that location or the feature can be the combination of the vascular structure and the part of the medical device at that location.

According to example, the image data representative of the location of the part of the medical device comprises fluorescence image data.

In an example, fluoroscopic low-dose X-ray surveillance is used to determine the location of the part of the medical device.

In an example, the position of the part of the medical device is at the position of a stenosis and the stenosis is then spatially localized on a fluoroscopic (fluoro) image, for example by markers detection; for example by detecting balloon markers over the image, for a balloon located at the position of a stenosis.

For example, image data representative of the location of the part of the medical device comprises an inflated balloon. In an example, the inflated balloon contains contrast agent, and the fluorescence image data shows the inflated balloon containing contrast agent.

In an example, the at least one first image is "non-injected", meaning that contrast agent is or has not been injected at the time of image acquisition, but with the position of the stenosis visible or able to be determined because of the part of the medical device. For example, for the at least one first image a patient's vasculature can be invisible, or in other words not visible and distinct. However, the at least one second image is injected, meaning that contrast agent is or has been injected at the time of image acquisition, but with the position of the stenosis not visible. For example, for the at least one second image a patient's vasculature is visible and distinct. However, this does not mean that every at least one first image has to be acquired as a low X-ray dose fluorescence image. The at least one first image can be a high X-ray dose (angiography) image, but without contrast agent.

According to an example, the vascular treatment was applied at a time corresponding to a time of acquisition of the at least one first image, and the method 10 further comprises the following:

In a determining step 16, also referred to a step c), a determining from the at least one first image that the vascular treatment was applied at the time of acquisition of the at least one first image.

In an example, step c) comprises determining the time when the vascular treatment was applied.

In an example, the at least one first image comprises an image acquired at the time of the vascular treatment and a further image acquired at a different time to the time of the vascular treatment. Step c) then comprises determining which of the at least one first image was acquired at the time of the vascular treatment; for example, through determining which image comprises a feature such as an enlarged region or feature at a particular location.

In an example, the at least one first image comprises an image acquired at the time of the vascular treatment and more than one further image, each further image acquired at a different time to the time of the vascular treatment. Step c) then comprises determining which of the at least one first image was acquired at the time of the vascular treatment. For example, through determining which image comprises a feature such as a difference with respect to the other images at a particular location.

In an example, the determining is achieved with the part of the medical device in one of the states associated with a phase of the vascular treatment.

For example, by determining the time when the vascular treatment was applied, it can be determined whether the at least one second image was acquired before or after the time of the vascular treatment, or that the vascular treatment was applied at the time of acquisition of the at least one second image. In other words, the at least one second image can be automatically placed into temporal context with respect to the vascular treatment.

In an example, the actual time of acquisition of the at least one first image is not required to be determined. For example, the at least one first image and the at least one second image can be acquired and saved in a temporal sequence. Determining the at least one first image when the vascular treatment was applied enables the earlier images in the sequence to be delineated as pre-treatment, and the later images in the sequence to be delineated as post-treatment. In this delineation, the actual time of acquisition of images is not required to be known, because the images themselves were temporally ordered.

In an example, the outputting of data representative of the vascular structure at the determined location comprises information on a stenosis that has been treated. For example, the vascular treatment was applied at the location of a stenosis. In another example, the outputting of data representative of the vascular structure at the determined location comprises information on a stenosis that is to be treated. In another example, the outputting of data representative of the vascular structure at the determined location comprises information on a stenosis that had been treated. For example, the vascular treatment is to be applied at the location of a stenosis.

For example, the outputting of data can comprise the location of a treated stenosis presented on a schematic graph of the coronary arteries. For example, the location of the treated stenosis can be presented on the at least one first image or, in addition or alternatively, on the at least one second image. In an example, QCA values can be associated with the treated stenosis presented on the schematic graph.

In an example, it can be difficult to determine which coronary branch (its anatomical name) has been treated, and the clinician clicks on the schematic graph in order to provide this information.

In an example, the outputting of data representative of the vascular structure at the determined location comprises a Quantitative Coronary Angiography (QCA) of a stenosis before stenting. In an example, the outputting of data comprises a QCA of a stenosis after stenting. Here, the QCA is the relative reduction of, for example, an artery diameter at the stenosis position.

In an example, known tools are used to digitally compute the QCA from one angiographic frame. For example, the QCA is determined from the at least one second image. In other words, QCA values associated with a stenosis can be presented pre and post intervention.

In an example, a list of QCA values associated with different stenosis is presented pre and post intervention, where the location of a vascular treatment is at the location of a stenosis.

According to an example, the vascular treatment comprises the part of the medical device being moved from a non-deployed state to a deployed state, and the at least one first image comprises image data representative of the part of the medical device in a state other than the non-deployed state.

In an example, step d) comprises determining from the at least one first image that the part of the medical device is in a state other than the non-deployed state.

In an example, step c) comprises determining from the at least one first image that the part of the medical device is in a state other than the non-deployed state.

In other words, determination that the medical device is in any state other than a non-deployed state indicates that the medical device is being deployed, even if it has not been fully deployed. This information can be used to determine that the vascular treatment is being applied at that time and be used to determine the location of the deployment and therefore the location of the vascular structure at the determined location.

In other words, deployment of the medical device can be used to determine the location of the feature and determine the time of the vascular treatment. Or, to put it another way, the deployment of the medical device can place the at least one second image into spatial and temporal context with respect to an anomaly or stenosis and its treatment.

In an example, image data associated with the deployment of the medical device has a signature and this signature can be used to determine that the medical device has been deployed. In an example, the part of the medical device comprises a balloon. For example, the signature can be the balloon being in an inflated state or partially inflated state.

In an example, the location of the vascular treatment and the location of the feature is determined by detecting the location of where the balloon was inflated in the at least one first image.

In an example, the time of the vascular treatment is determined by determining the at least one first image corresponding to when the balloon was inflated.

In an example, the at least one first image is acquired in the manner of an angiogram, where contrast agent has been injected into at least a part of the vascular structure during acquisition of the image, but where the at least one first image comprises signature image data associated with deployment of the medical device. In other words, the method can involve an imaging system acquiring a number of similar images. At the time contrast agent is injected, these images are acquired as second image(s) and at the time when no (or little) contrast agent is injected these images are acquired as first image(s). However, when images are acquired when contrast agent is injected, and which also exhibit signature image data associated with deployment of the part of the medical device. these images are acquired as first image(s). In other words, this image is a first image, because it can be used to determine both the spatial location of the feature (the position of the balloon deployment) and the time of vascular treatment (the image corresponds to a time of the balloon deployment). Therefore, advantageously, the same X-ray device or system can be utilized for obtaining the first and the second images, with these images being differentiated on the basis of whether contrast agent was present or not.

In an example, a fluoroscopic low-dose X-ray device is used to acquire the first images and a different device such as an X-Ray CT scanner is used to acquire the second images.

Figure 2:
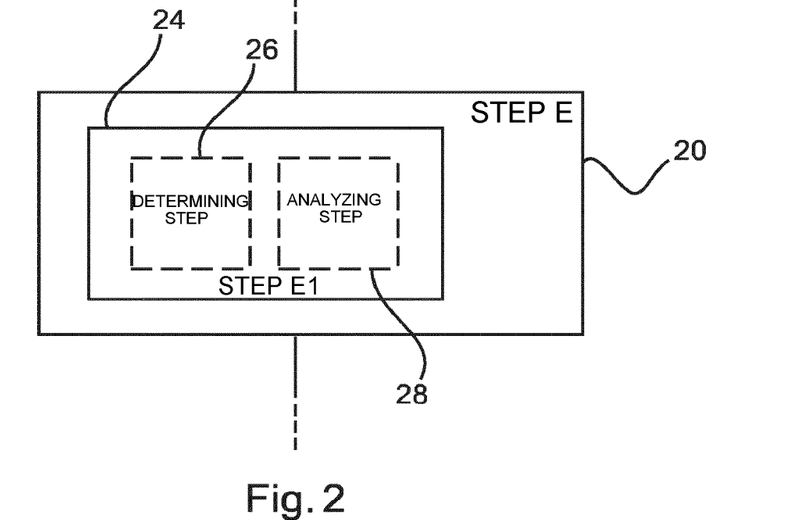
FIG. 2 shows an example of a method step involved in a method for automatic quantification of a part of a vascular structure.

FIG. 2 shows an example of a method step 20, step e), involved in a method for automatic quantification of a part of a vascular structure. According to an example, step e) of the method comprises:

In an aligning step 24, also referred to as step e1), the spatial representation of the region of interest of the vascular structure in the at least one first image is aligned with the spatial representation of the region of interest of the vascular structure in the at least one second image.

In an example, the vascular treatment was applied at a time corresponding to a time of acquisition of the at least one first image.

In an example, the aligning is achieved by cardiac road-mapping. For example, a position in a fluoroscopic image is translated into a position into the corresponding angiographic images, where those angiographic images can have been acquired both before and after intervention. For example, the aligning can be used in determining the transform.

In an example, at least some features (e.g. A, B, C) in the at least one first image are aligned with, or projected onto, at least some similar features (e.g. A', B', C') in the at least one second image.

In an example, the aligning may comprise the region of interest of the at least one first image being placed over the top of the region of interest of the at least one second image.

In an example, the tip of the guidewire or balloon markers are used as part of the aligning. In another example, the tip of the guidewire and the balloon markers are used as part of the aligning.

In an example, the aligning accounts for the patient's cardiac cycle or, in addition or alternatively, for the breathing cycle.

In an example, the aligning may comprise the step of warping the region of interest of the at least one first image or, in addition or alternatively, the region of interest of the at least one second image.

In an example, acquisition of the at least one first image is performed at the same angulation as that used for acquisition of the at least one second image. For example, both acquisitions are performed with the same C-arm angulation. This provides for ease of aligning the images.

In an example, the aligning leads to a spatial matching of the region of interest of the at least one first image with the region of interest of the at least one second image.

According to an example, step e1) of the method further comprises: In determining step 26, a region of reduced vessel radius in a region in or around the determined location in the spatial representation of the region of interest of the part of the vascular structure of the at least one second image is determined.

This provides for fine-tuning of the aligning process, for example if the stenosis position translated from its detection in fluoro (fluoroscopy), and the angio/fluoro matching (angiography/fluoroscopy matching) is not as accurate as required.

According to an example, the at least one first image comprises image data representative of the part of a medical device located within a part of the vascular structure. In this example, step e1) of the method further comprises: In an aligning step 28, the image data, which is representative of the part of the medical device located within the part of the vascular structure in the at least one first image, is aligned with the spatial representation of the region of interest of the part of the vascular structure in the at least one second image. For example, the aligning can be used in determination of the transform.

In an example, angio/fluoro matching can be performed by aligning the interventional objects visible in the fluoro, with the vasculatures visible in the angio.

For example, imagery of the guidewire within the vascular structure of the at least one first image can be aligned with the observable vascular structure in the at least one second image.

Figure 3:
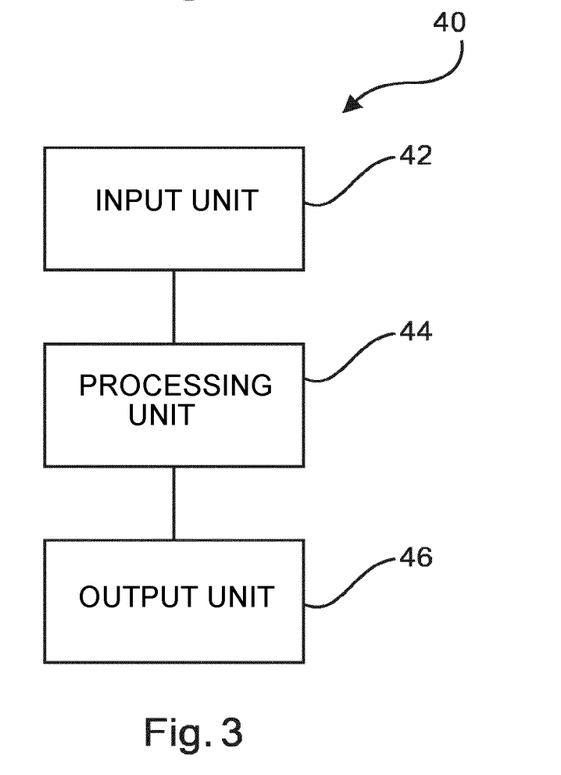
FIG. 3 shows a schematic set up an example of an apparatus for automatic quantification of a part of a vascular structure.

FIG. 3 shows an example of an apparatus 40 for automatic quantification of a part of a vascular structure. The apparatus comprises an input unit 42, a processing unit 44; and an output unit 46. The input unit 42 is configured to provide the processing unit 44 with at least one first image comprising a spatial representation of a region of interest of a vascular structure. The at least one first image comprises image data representative of a location of a part of a medical device. The medical device is configured to be used in a vascular treatment, and the part of the medical device is configured to be in a plurality of states associated with different phases of the vascular treatment. The input unit 42 is further configured to provide the processing unit 44 with at least one second image comprising a spatial representation of the region of interest of the vascular structure. The at least one second image comprises image data representative of at least a part of the vascular structure in a visible and distinct manner. The processing unit 44 is further configured to determine a location of a feature in the spatial representation of the region of interest of the vascular structure of the at least one first image. The feature is associated with the part of the medical device in one of the states associated with a phase of the vascular treatment. The processing unit 44 is further configured to determine a transform relating at least one location in the at least one first image to a corresponding at least one location in the at least one second image, and apply the transform to the location of the feature in the spatial representation of the region of interest of the vascular structure of the at least one first image to provide a determined location in the spatial representation of the region of interest of the vascular structure of the at least one second image. The output unit 46 is configured to output data representative of the vascular structure at the determined location.

In an example, the processing unit is configured to determine the location of the image data representative of the location of the part of the medical device in one of the states associated with a phase of the vascular treatment in the at least one first image. In this manner, the processing unit can determine the location of the feature in the spatial representation of the region of interest of the vascular structure of the at least one first image.

In an example, the image data representative of the location of the part of the medical device comprises non-injected X-ray data.

In an example, the non-injected X-ray data comprises fluorescence image data.

In an example, the image data representative of the location of the part of the medical device comprises fluorescence image data.

In an example, the processing unit is configured to determine the location through the use of an image processing unit.

In an example, the processing unit is configured to determine and apply the transform through the use of the image processing unit.

In an example, the at least one second image was acquired before a vascular treatment was applied. This enables for example pre intervention QCA values to be determined.

In an example, the at least one second image was acquired after a vascular treatment was applied. This enables for example post intervention QCA values to be determined.

In an example, the at least one second image was acquired at the time a vascular treatment was applied. This enables for example intervention QCA values to be determined.

In an example, the at least one second image comprises images acquired both before and after the vascular treatment was applied. This enables for example the success of the intervention to be determined from QCA values; or in other words, to be able to qualify the intervention outcome.

In an example, the at least one second image comprises images acquired both before and at the time the vascular treatment was applied. This enables for example QCA values to be used to determine whether the intervention was deployed as expected.

In an example, the at least one second image comprises images acquired both at the time of and after the vascular treatment was applied. This enables for example, it to be determined whether intervention was deployed as expected and whether the post intervention vascular structure is as expected.

In an example, the processing unit is configured to correlate the location of the feature in the spatial representation of the region of interest of the vascular structure of the at least one first image with a correlated location in the spatial representation of the region of interest of the vascular structure of the at least one second image In an example, the at least one second image comprises images acquired both before and after and at the time the vascular treatment was applied. This enables a complete picture or understanding of the stenosis and the intervention to be determined.

In an example, the part of the medical device comprises a balloon.

According to an example, the vascular treatment was applied at a time corresponding to a time of acquisition of the at least one first image. In this example, the processing unit is configured to determine from the at least one first image that the vascular treatment was applied at the time of acquisition of the at least one first image.

In an example, the processing unit is configured to determine the time when the vascular treatment was applied.

By determining the time when the vascular treatment was applied, it can be determined whether the at least one second image was acquired before or after the time of the vascular treatment, or that the vascular treatment was applied at the time of acquisition of the at least one second image. In other words, the at least one second image can be automatically placed into temporal context with respect to the vascular treatment.

In an example, the vascular treatment comprises the part of the medical device being moved from a non-deployed state to a deployed state, and the at least one first image comprises image data representative of the part of the medical device in a state other than the non-deployed state. In this example, the processing unit is configured to determine from the at least one first image that the part of the medical device is in a state other than the non-deployed state. In this example, the processing unit is configured to determine from the at least one first image that the part of the medical device is in a deployed state.

According to an example, the processing unit is configured to align the spatial representation of the region of interest of the vascular structure in the at least one first image with the spatial representation of the region of interest of the vascular structure in the at least one second image in order to determine and apply the transform.

In an example, the processing unit is configured to determine a region of reduced vessel radius in a region in or around the determined location in the spatial representation of the region of interest of the part of the vascular structure of the at least one second image.

In an example, the at least one first image comprises image data representative of a part of a medical device located within a part of the vascular structure. In this example, the processing unit is configured to align the image data representative of the part of the medical device located within the part of the vascular structure in the at least one first image with the spatial representation of the region of interest of the part of the vascular structure in the at least one second image.

In an example, the processing unit is configured to align the spatial representation of the region of interest of the vascular structure in the at least one first image with the spatial representation of the region of interest of the vascular structure in the at least one second image. This is done in order to correlate the location of the feature in the spatial representation of the region of interest of the vascular structure of the first image with the correlated location in the spatial representation of the region of interest of the vascular structure of the at least one second image.

In an example, the feature comprises an anomaly such as a stenosis.

In an example, the at least one second image comprises an angiogram.

In an example, the at least first image and the at least one second image are acquired at the same angulation.

Figure 4:
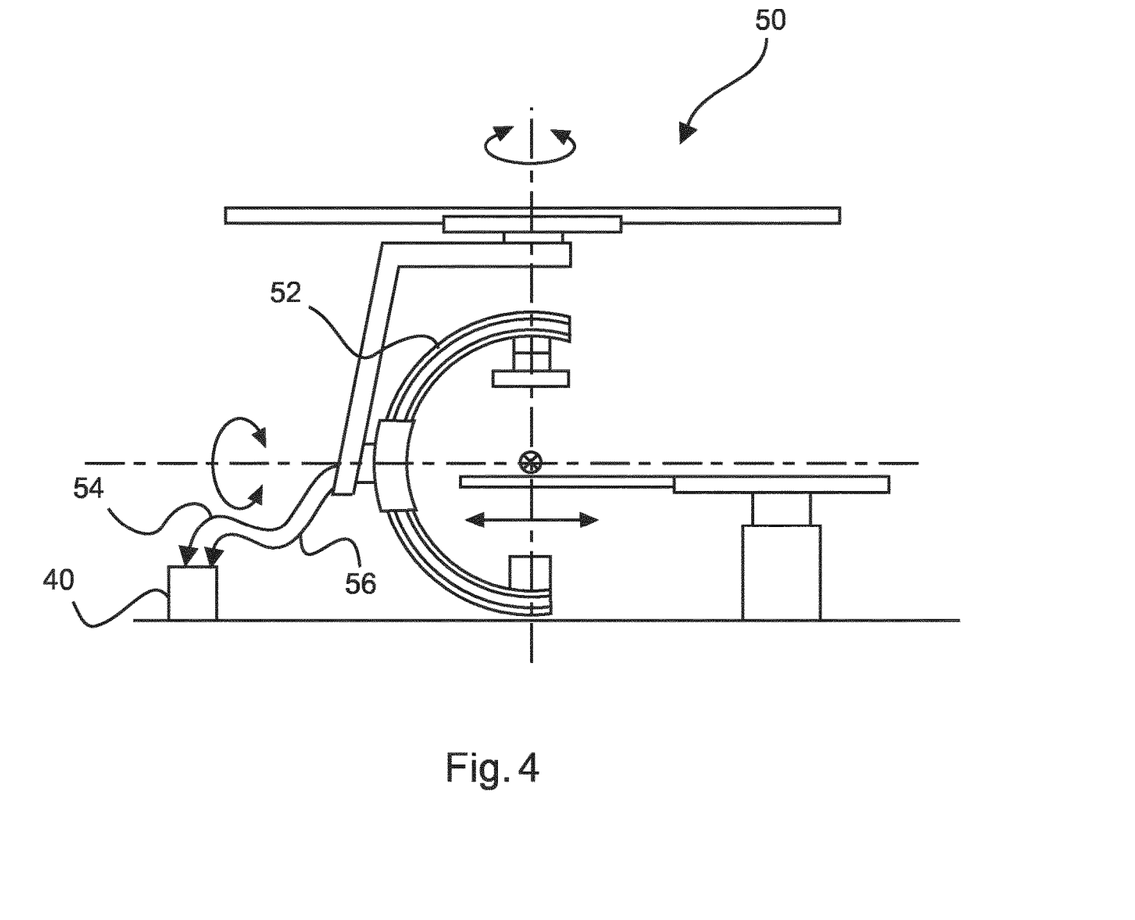
FIG. 4 shows a schematic set up an example of a medical imaging system for automatic quantification of a part of the vascular structure.

FIG. 4 shows a medical imaging system 50 for automatic quantification of a part of the vascular structure. The system comprises at least one image acquisition unit 52, and an apparatus 40 for automatic quantification of a part of a vascular structure. The apparatus 40 is provided as an application according to the above-mentioned FIG. 3. The at least one image acquisition unit 52 is configured to provide the at least one first image comprising the spatial representation of the region of interest of the vascular structure. The at least one image acquisition unit 52 is also configured to provide the at least one second image comprising the spatial representation of the region of interest of the vascular structure. The image acquisition unit 52 is shown as a C-arm angulation arrangement; however in other examples, different types of image acquisition units are used.

In an example, the at least one image acquisition unit comprises an X-ray imaging device, for example, a CT arrangement. For example, the at least one image acquisition unit comprises a C-arm CT system. In an example, the at least one image acquisition unit comprises an interventional X-ray system.

In an example, the at least one image acquisition unit comprises a fluoroscopic imaging device. For example, a fluoroscopic low-dose X-ray device.

In an example, the same image acquisition unit is configured to provide the at least one first image and the at least one second image.

In an example, the output data representative of the vascular structure at the determined location comprises information on a stenosis that is to be treated or that has been treated.

In an example, the output data is useable to enable a clinician to determine the size of a stent before its deployment.

In an example, the output data is useable to enable a clinician to determine whether the vascular treatment of intervention was successful.

In an example, the system is used for at least one of the group of: Percutaneous Transluminal Coronary Angioplasty (PTCA) and Percutaneous Coronary Intervention (PCI) in catheter laboratories, to treat cardiac stenosis.

By providing a medical system for automatic quantification of a part of a vascular structure, such as at the location of an anomaly or stenosis, pre and post intervention, the clinician is automatically provided with the required reporting information associated with the intervention. The clinician is provided with information regarding which stenosis was treated, and where that stenosis is located within the vascular structure. The clinician is provided with information regarding the severity of a stenosis prior to the intervention, and whether the intervention has been successful. The clinician does not need to manually determine QCA values relating to the intervention, which would require a manual determination of when the intervention was performed and assessing angiography image frames both before and after that intervention, and which would also require a manual determination of where the intervention was performed within those images.

In an example, the at least one first image comprises a plurality of images and the at least one second image comprises a plurality of images, and a number of vascular treatments were undertaken at different times, each vascular treatment associated with a feature or anomaly in the vascular structure (such as a stenosis), and the apparatus for automatic quantification of a part of a vascular structure is configured to output data representative of the different stenosis.

Figure 5:
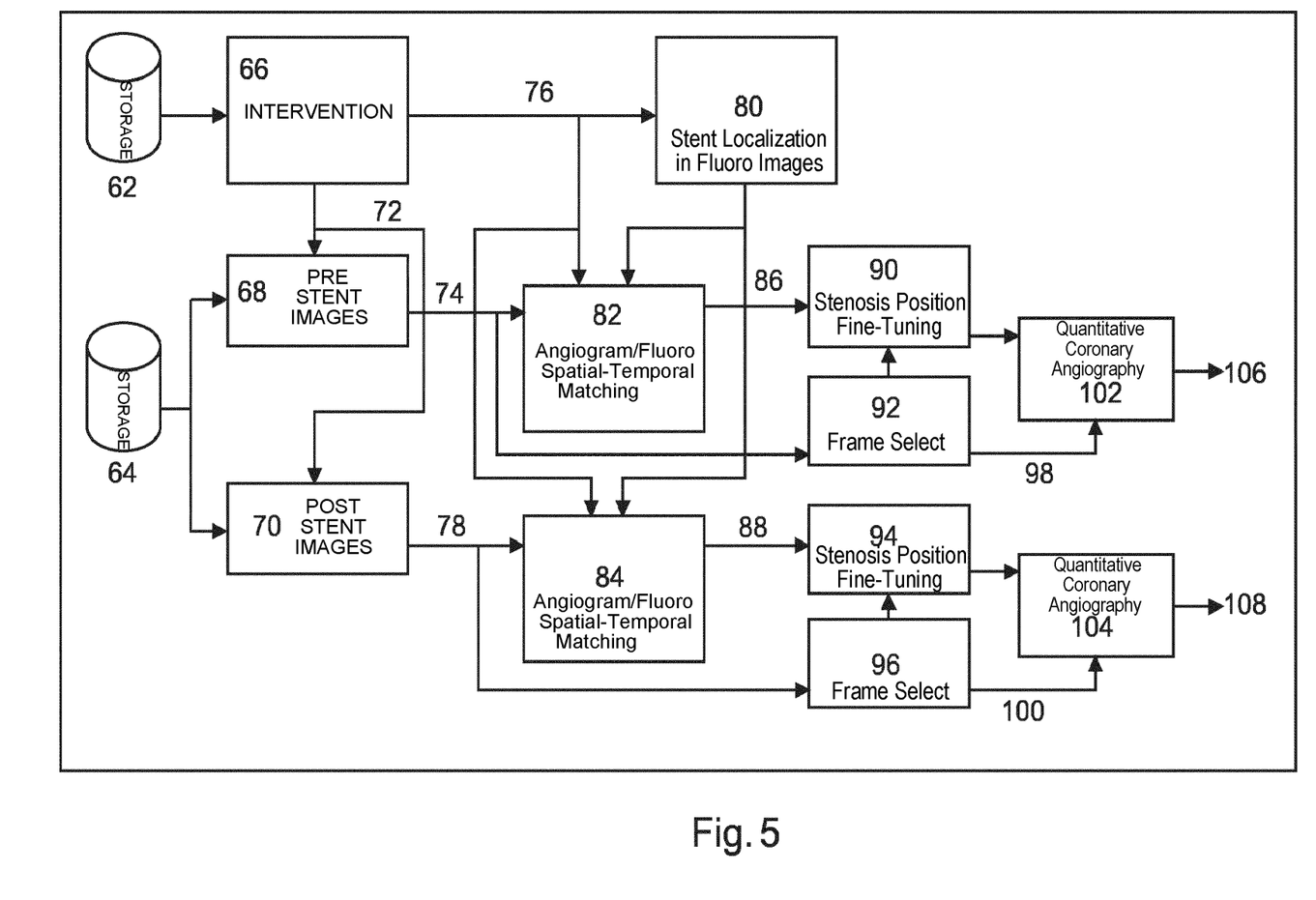
FIG. 5 shows an illustration of an example of a workflow of a method for automatic quantification upper part of the vascular structure.

FIG. 5 shows a further example of a detailed workflow. Fluoroscopic images are stored in storage medium 62. Angiogram images are stored in storage medium 64. At box 66 there is indicated an intervention, such as a stent deployment event. Stent deployment event 66 is usable to separate angiogram images into angiogram images pre-stenting 68, and into angiogram images post-stenting 70. Separation of angiograms 68 also involves selection of those images where the vascular structure in shown in a visible and distinct manner, for example when contrast agent was suitably injected into the vascular structure. Separation of angiograms 70 also involves selection of those images where the vascular structure in shown in a visible and distinct manner, for example when contrast agent was suitably injected into the vascular structure. Arrow 72 indicates that the time of image acquisition, and the C-arm angulation can be correlated with respect to images 68 and 70. Arrow 76 indicates a fluoro sequence during stent deployment, which at box 80 is used for stent localization in fluoro images. At box 82 the fluoro sequence 76, along with the stent localization in fluoro, i.e. box 80, is used in combination with angiogram images pre-stenting 68 provided as an angiogram sequence pre-dilation (in an example at the same angulation) 74 to provide for angiogram/fluoro spatial-temporal matching (cardiac road-mapping) with respect to pre-stenting imagery. At box 84 the fluoro sequence of arrow 76, along with the stent localization in fluoro, i.e. the box 80, is used in combination with the angiogram images post-stenting 70 provided as an angiogram sequence post-dilation (in an example at the same angulation) 78 to provide for angiogram/fluoro spatial-temporal matching (cardiac road-mapping) with respect to pre-stenting imagery. At an arrow 86, from the angiogram/fluoro spatial-temporal matching 82, a rough stent position on the angio (angiography) image 86 may be provided with respect to pre-dilation imagery. Similarly at an arrow 88, from the angiogram/fluoro spatial-temporal matching 84, a rough stent position on the angio image 86 may be provided with respect to post-dilation imagery. The pre-dilation sequence 74 undergoes a frame selection 92. This is because it can be that the stenosis position translated from its detection in fluoro and the angiogram/fluoro matching is not perfectly accurate. At box 90, stenosis position fine-tuning in the angiogram image is carried out. Frame selection 92 is conducted looking in the angiogram imagery for a reduced vessel radius in the vicinity of the rough stent location 86, in order to provide the fine-tuning 90 in the pre-dilation imagery. Similarly, the post-dilation sequence 78 undergoes a frame selection 96, which in combination with a rough stent position on the angiogram 88 can be used to provide for a stenosis position fine-tuning 94 in the angiogram imagery post-dilation. An arrow 98 relates to pre-stenting angiogram imagery, which in combination with the fine-tuning of the stenosis position 90 can be used at box 102 to automatically provide Quantitative Coronary Angiography (QCA) values at the position of the stenosis before stenting 106. Similarly arrow 100 relates to pre-stenting angiogram imagery, which in combination with the fine-tuning of the stenosis position 94 can be used at box 104 to automatically provide Quantitative Coronary Angiography (QCA) values at the position of the stenosis after stenting 108.

In another exemplary embodiment, a computer program or computer program element is provided that is characterized by being configured to execute the method steps of the method according to one of the preceding embodiments, an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus comprising:
an input unit;
a processing unit; and
an output unit;
wherein the input unit is configured to provide the processing unit with at least one first image comprising a spatial representation of a region of interest of a vascular structure, wherein the at least one first image comprises image data representative of a location of a part of a medical device, to be used in a vascular treatment, wherein the part of the medical device is a balloon configured to be in a plurality of states associated with different phases of the vascular treatment, wherein the image data has a signature indicating an at least partially inflated state of the balloon;
wherein the input unit is configured to provide the processing unit with second images each comprising a spatial representation of the region of interest of the vascular structure, wherein the second images each comprise image data acquired with contrast agent present, in which at least a part of the vascular structure is represented in a visible and distinct manner, wherein the second images include images acquired both before and after the vascular treatment was applied;
wherein the processing unit is configured to i) determine a time of acquisition of the at least first one image as a time of the vascular treatment and ii) determine, in the at least one first image, a location of the signature;
wherein the processing unit is configured to determine a transform relating at least one location in the at least one first image to a corresponding at least one location in at least one of the second images, and apply the transform to a location of the signature feature in the at least one first image to provide a corresponding location in the at least one second image, and
wherein the output unit is configured to output data representative of the vascular structure at the determined location in the at least one second image, wherein the output data comprises information qualifying an outcome of the vascular treatment.

2. The apparatus of claim 1, wherein the processing unit is configured to align the spatial representation of the region of interest of the vascular structure in the at least one first image with the spatial representation of the region of interest of the vascular structure in the at least one second image in order to determine and apply the transform.

3. The apparatus of claim 1, further comprising:
at least one image acquisition unit,
wherein the at least one image acquisition unit is configured to provide the at least one first image comprising the spatial representation of the region of interest of the vascular structure, and to provide the second images comprising the spatial representation of the region of interest of the vascular structure.

4. A method, comprising
a) providing at least one first image comprising a spatial representation of a region of interest of a vascular structure, wherein the at least one first image comprises image data representative of a location of a part of a medical device to be used in a vascular treatment, wherein the part of the medical device is a balloon configured to be in a plurality of states associated with different phases of the vascular treatment, the image data having a signature indicating an at least partially inflated state of the balloon;
b) providing second images each comprising a spatial representation of the region of interest of the vascular structure, wherein the second images each comprise image data acquired with contrast agent present, in which at least a part of the vascular structure is represented in a visible and distinct manner, wherein the second images include images acquired both before and after the vascular treatment was applied;
c) determining a time of acquisition of the at least first one image as a time of the vascular treatment;
d) determining in the at least one first image, a location of the signature;
e) determining a transform relating at least one location in the at least one first image to a corresponding at least one location in the at least one of the second images, and applying the transform to the signature location to provide a corresponding location in the at least one second image; and
f) outputting of data representative of the vascular structure at the determined location in the at least one second image, wherein the output data comprises information qualifying an outcome of the vascular treatment.

5. The method of claim 4, wherein the image data of the at least one first image comprises non injected X-ray data, wherein contrast agent is not present at the time of acquisition.

6. The method of claim 4, wherein step e) comprises aligning the spatial representation of the region of interest of the vascular structure in the at least one first image with the spatial representation of the region of interest of the vascular structure in the at least one second image.

7. The method of claim 6, wherein aligning the spatial representation of the region of interest of the vascular structure in the at least one first image with the spatial representation of the region of interest of the vascular structure in the at least one second image further comprises determining a region of reduced vessel radius in a region in or around the determined location in the at least one second image.

8. A tangible computer-readable medium having stored thereon non-transitory computer program instructions for controlling a device or a system, which, when executed by a processor is configured to carry out the method of claim 4.

9. The method of claim 4, wherein the vascular treatment is the deployment of a stent, the method further comprising separating the second images into pre-stenting images and post-stenting images.

10. The method of claim 4, wherein the signature comprises an inflated balloon containing contrast agent.

11. The method of claim 6, wherein the aligning is achieved by cardiac road-mapping.

* * * * *